(12) United States Patent
Doyle

(10) Patent No.: US 10,034,720 B2
(45) Date of Patent: Jul. 31, 2018

(54) OVERFORCE MECHANISM

(75) Inventor: Mark Doyle, Del Mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 1630 days.

(21) Appl. No.: 13/521,197

(22) PCT Filed: Jan. 26, 2011

(86) PCT No.: PCT/US2011/022562
§ 371 (c)(1),
(2), (4) Date: Nov. 15, 2012

(87) PCT Pub. No.: WO2011/094299
PCT Pub. Date: Aug. 4, 2011

(65) Prior Publication Data
US 2013/0053833 A1 Feb. 28, 2013

Related U.S. Application Data

(60) Provisional application No. 61/298,784, filed on Jan. 27, 2010.

(51) Int. Cl.
*A61B 34/00* (2016.01)
*A61B 17/00* (2006.01)
*A61B 90/00* (2016.01)

(52) U.S. Cl.
CPC ........... *A61B 34/70* (2016.02); *A61B 34/77* (2016.02); *A61B 2017/00477* (2013.01);
(Continued)

(58) Field of Classification Search
CPC ........... A61B 2017/00477; A61B 2017/00539; A61B 2090/031; A61B 2090/064; A61B 34/70; A61B 34/77
(Continued)

(56) References Cited

U.S. PATENT DOCUMENTS 5,031,606 A * 7/1991 Ring, Sr. ............... A61F 5/0125
602/16
5,190,042 A * 3/1993 Hock ..................... A61B 3/16
600/405
(Continued)

FOREIGN PATENT DOCUMENTS

DE 4106468 C1 * 3/1992 ........... B23B 31/086
EP 2074971 A1 7/2009
WO WO 2008/121234 A2 10/2008

OTHER PUBLICATIONS

Espacenet English Translation of DE 4106468 C1.*
European Search Report and Written Opinion issued in European Patent No. EP11737566 dated Mar. 10, 2017.

*Primary Examiner* — Gary Jackson
*Assistant Examiner* — Jonathan Kuo
(74) *Attorney, Agent, or Firm* — Arent Fox LLP

(57) ABSTRACT

An overforce mechanism comprising a driving assembly, a driven assembly, and a variably engageable coupling, shunts or dampens a motion of a control cylinder for a hydraulic device when that motion exceeds a predefined, unsafe threshold. The overforce mechanism avoids or reduces damage either to the device itself, to ancillary devices and/or to the patient. In an aspect, the variably engageable coupling may include a biasing mechanism and a coupling member, wherein the biasing mechanism automatically resets or releases upon reaching a force or tension threshold. Further, the overforce driven assembly may include an overforce rod that allows the force or motion to be channeled away from the source. The variably engageable coupling may comprise a dowel and spring mechanism that automatically resets with tension.

25 Claims, 11 Drawing Sheets

(52) U.S. Cl.
CPC ............... *A61B 2017/00539* (2013.01); *A61B 2090/031* (2016.02); *A61B 2090/064* (2016.02)

(58) Field of Classification Search
USPC ............. 403/321–330; 606/1; 901/49, 11–12
See application file for complete search history.

(56) References Cited

U.S. PATENT DOCUMENTS

| | | | | |
|---|---|---|---|---|
| 5,273,519 | A | * | 12/1993 | Koros ................ A61B 17/1611 606/170 |
| 5,431,645 | A | | 7/1995 | Smith et al. |
| 6,458,142 | B1 | | 10/2002 | Faller et al. |
| 7,288,098 | B2 | | 10/2007 | Huitema et al. |
| 7,470,268 | B2 | | 12/2008 | Doyle et al. |
| 2002/0111604 | A1 | * | 8/2002 | Doyle .................... A61B 34/37 606/1 |
| 2007/0267281 | A1 | | 11/2007 | Smith |
| 2008/0083813 | A1 | | 4/2008 | Zemlok et al. |
| 2008/0103437 | A1 | * | 5/2008 | Duchon ................ A61B 6/481 604/67 |

* cited by examiner

OVERFORCE MECHANISM

This application claims priority to U.S. Provisional Patent Appl. No. 61/298,784 filed on Jan. 27, 2010. This application is also related to Applicant's co-pending PCT Appl. No. PCT/US2011/022086 titled "HYDRAULIC DEVICE INCLUDING A SPOOL VALVE" filed on Jan. 21, 2011 and PCT application Ser. No. PCT/US10/46619 titled "ARTICULATED SURGICAL TOOL" filed on Aug. 25, 2010. The entirety of each of the proceeding applications is hereby incorporated by reference herein.

BACKGROUND

Field of the Invention

Aspects of the present invention relate to mechanical devices and overforce mechanisms used in mechanical devices.

Background of the Related Art

Laparoscopic surgical tools, as well as tools for other surgical procedures, are known. However, current laparoscopic surgical instruments typically have considerable limitations, including those relating to their capability to access portions of the body obstructed by organs or other impediments, difficulty in sterilizing such instruments, and limitations with structural configurations that are awkward and difficult to use. While such existing laparoscopic surgical instruments can perform invasive surgical procedures, the instruments are awkward to manipulate and perform complicated movements that are often necessary in surgery. In particular, such instruments can be difficult to manipulate around corners, obstacles and to use in obstructed or otherwise difficult to reach environments.

Moreover, existing laparoscopic surgical instruments typically use cables and hydraulic lines to manipulate the surgical tip of the instruments. Such tools can be expensive and difficult to clean and sterilize. Since the cleaning procedure must be performed after each use, any expense incurred can substantially add to the cost of use of the device. Alternatively, if disposable tools are used, this can add to the cost of the overall system. Further, disposable tools may be made from less robust materials than those meant for multiple uses, leading to increased potential of problems due to equipment malfunction and/or fracture.

Moreover, laparoscopic surgical instruments using cables and hydraulic lines to remotely manipulate the surgical tip of the instruments can be vulnerable to accidental misuse or user overcompensation, which sometimes may be due to a lack of direct tactile feedback. In particular, problems can arise when a user moves a control for a laparoscopic surgical device in such a way that can cause damage to the device itself, to ancillary devices and/or to the patient.

Thus, there is a need in the art for a hand-actuated, articulating surgical instrument that provides the user with an increased degree of freedom of motion but that also prevents damage to the device, to ancillary devices and/or to the patient.

SUMMARY

While discussion of the aspects of the present invention that follows uses surgery for an illustrative purpose, it should be appreciated that aspects of the present invention are not limited to surgery and may be used in a variety of other environments. For example, aspects of the present invention may be used in manufacturing, construction, assembly lines, handling and disposing of hazardous materials, underwater manipulations, handling high temperature materials, or any other environment where a user may be remote from the item being manipulated or may experience fatigue when operating a mechanical device.

In one aspect of the present invention, an overforce mechanism shunts or dampens the motion of a control cylinder for a hydraulic device when that motion exceeds a predefined, unsafe threshold. As such, the described overforce mechanism avoids or reduces damage to the device itself, to ancillary devices and/or to the patient. In an aspect, the overforce mechanism includes a ball and spring mechanism that automatically releases upon reaching a force or tension threshold. Further, the overforce mechanism may further include an overforce rod that allows the force or motion to be channeled away from the source.

In another aspect of the present invention, an overforce mechanism shunts or dampens the motion of a control cylinder for a hydraulic device when that motion exceeds a predefined, unsafe threshold. The overforce mechanism includes a dowel and spring mechanism as well as an overforce rod that allows the motion to be channeled away from the source.

In yet another aspect of the present invention, multiple overforce mechanisms are used for multiple components on the same device. The overforce mechanisms may, for example, be used on different mechanical controls or on controls for different aspects of mechanical operations of the device. The multiple overforce mechanisms may be identical, or they may vary substantially, depending on the particular application.

Aspects of the present invention may incorporate methods, features, and operations as shown and described in U.S. Pat. No. 6,607,475 to Doyle, et al., the entirety of which is incorporated herein by reference. However, it should be noted that aspects of the present invention are not limited in application to devices shown in U.S. Pat. No. 6,607,475 or in related patents and applications. In some aspects, the present invention provides an apparatus for controlling the micro-movements and macro-movements of hydraulically actuated devices, including an articulated surgical tool. In these aspects, the present invention may enhance the control and manipulation of the device.

Aspects of the present invention provide benefits and advantages that include the ability to prevent unwanted force and resulting damage to actuated systems. Thus, actuated systems can be made more robust and precision instrumentation can be used in environments that would otherwise compromise relatively delicate equipment.

Additional advantages and novel features relating to aspects of the present invention will be set forth in part in the description that follows, and in part will become more apparent to those skilled in the art upon examination of the following or upon learning by practice of aspects of the invention.

BRIEF DESCRIPTION OF THE DRAWINGS

Aspects of the present invention will become fully understood from the detailed description given herein below and the accompanying drawings, which are given by way of illustration and example only and thus not limited with respect to aspects of the present invention, wherein.

DETAILED DESCRIPTION

Aspects of the present invention will now be described more fully hereinafter with reference to the accompanying drawings, in which variations and aspects of the present invention are shown. Aspects of the present invention may, however, be realized in many different forms and should not be construed as limited to the variations set forth herein; rather, the variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Figure 1A:
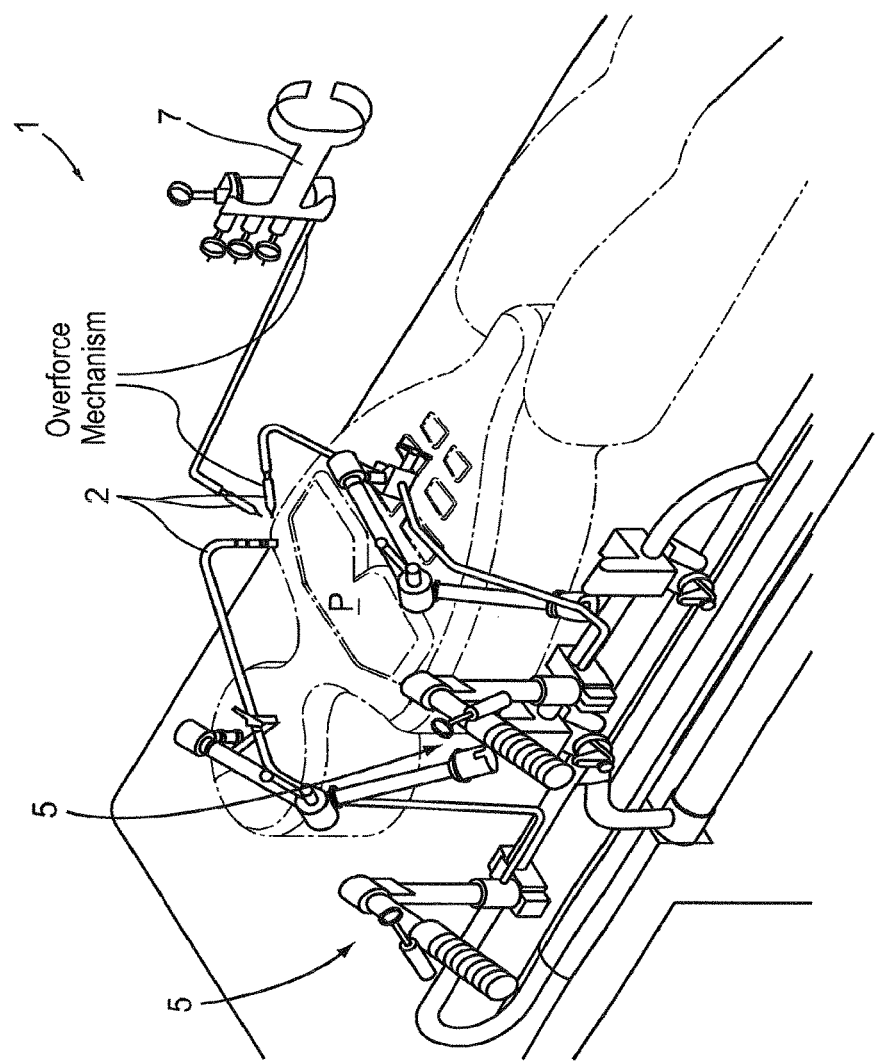
FIG. 1A is a diagram of an exemplary system for use in accordance with aspects of the present invention.

FIG. 1A is a diagram of an exemplary system of an overforce mechanism of aspects of the present invention that may be utilized in performing surgery on a patient P. Device 1 is described in more detail in U.S. Pat. No. 6,607,475, the entirety of which is incorporated herein by reference. Device 1 may include any number of suitable hydraulically driven mechanical devices to assist in the performance of surgery, maintenance and/or other mechanical operations. Although FIG. 1A shows a surgical device 1, it is to be understood that variations of aspects of the present invention can be used in conjunction with any suitable device with mechanical actuating features. Some of the hydraulically driven mechanical devices, such as the one shown in FIG. 1A, may contain control portions with a single control cylinder 5 or control portions with multiple control cylinders 7. The control portions with single or multiple control cylinders may serve to allow a user, such a surgeon, to actuate mechanical operations in another portion of the device. For example, the control portions with a single or multiple control cylinders may actuate and move various tools 2 for performing of surgery.

Figure 1B:
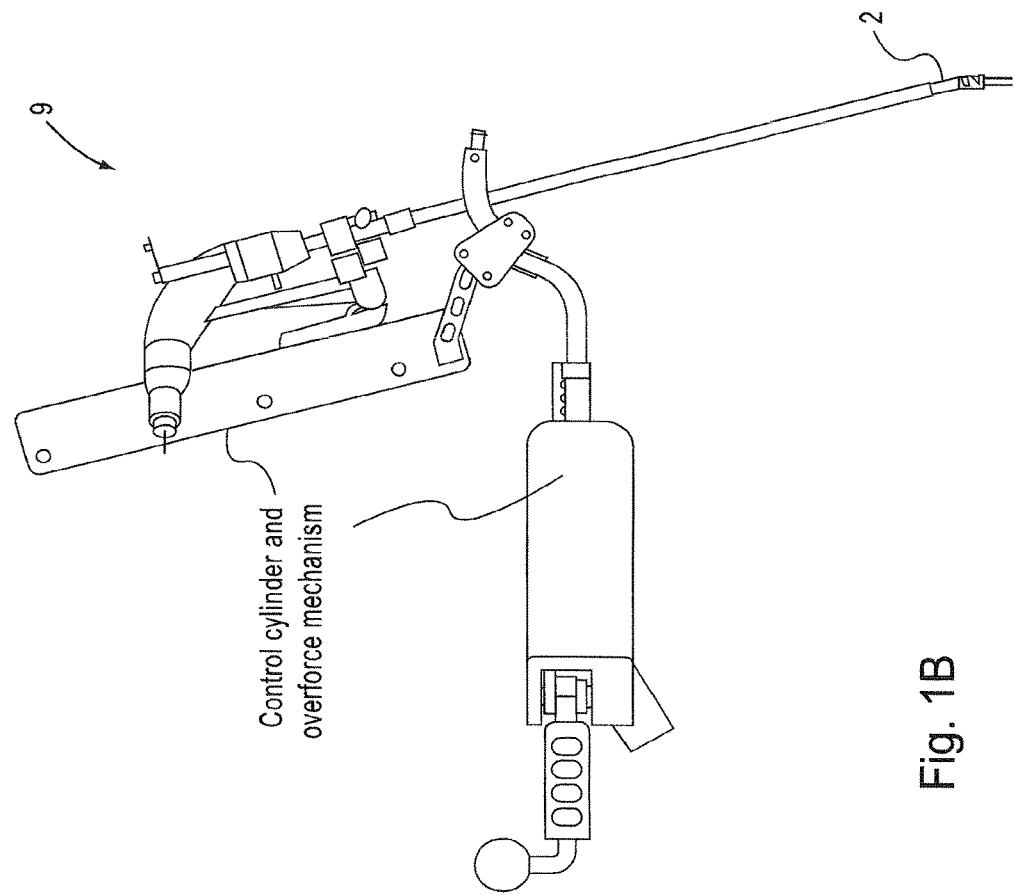
FIG. 1B is a diagram of a variation of the slave portion of a device that may be used in alternative to the slave portion of the device shown in FIG. 1A.

Generally speaking, the control portions (e.g., control portions with a single or multiple control cylinders) are part of the "control portion" of the device 1 and the various tools 2 are part of the "slave portion" of the device 1. FIG. 1B is a diagram of a variation of the slave portion of the device that may be used in alternative to the slave portion of the device shown in FIG. 1A. As shown in FIG. 1B, the slave portion 9 of the device includes various tools 2 that may be utilized for performing surgery and/or other mechanical operations. The connections between the control and slave portions may be primarily hydraulic, for example, to allow transmission of mechanical forces between the two portions. However, other connections (e.g., electrical, hydraulic, electromagnetic, cable, optical, etc.) may also be present in order to transmit various types of information, forces or motion between the control and slave portions of the device.

Figure 2A:
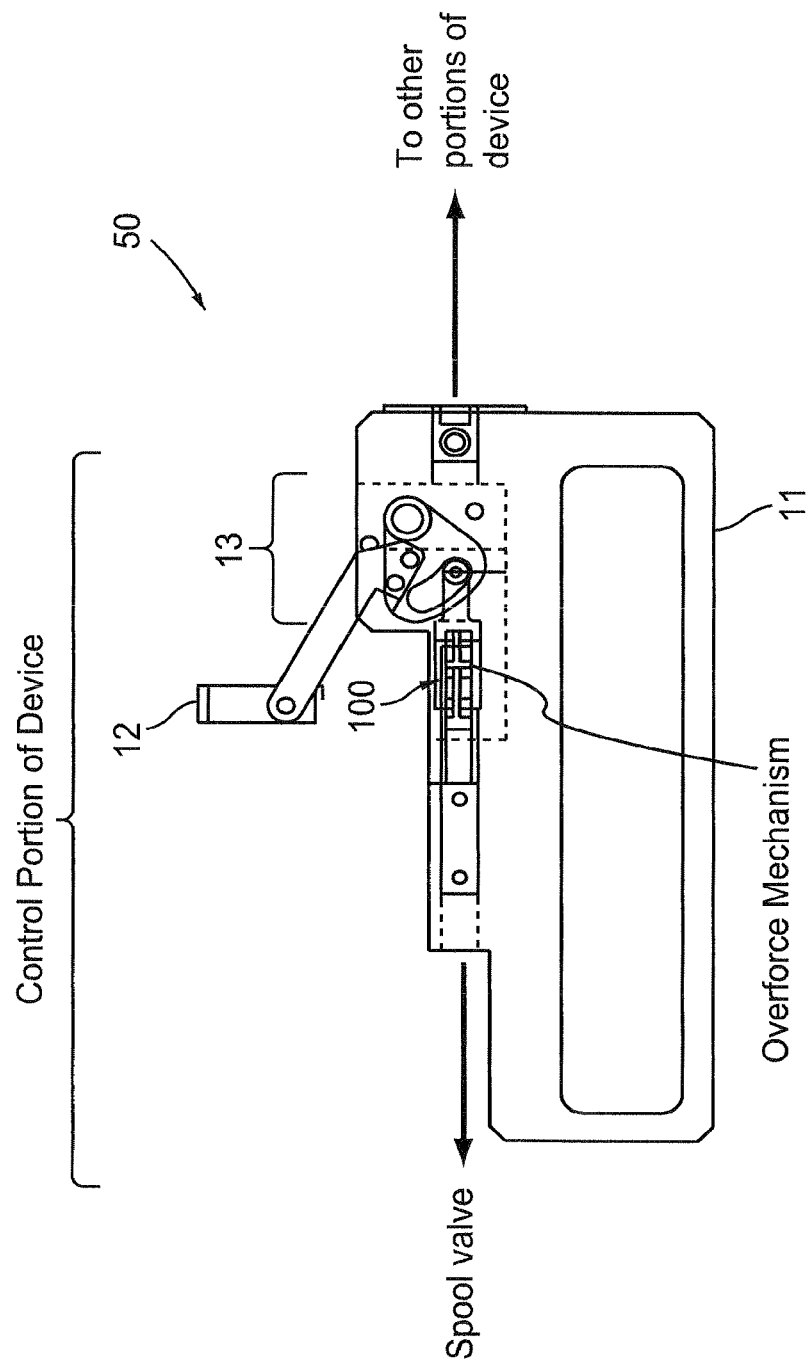
FIG. 2A is a detailed drawing of one aspect of an exemplary control unit that may be used in conjunction with aspects of the present invention.

FIG. 2A is a detailed drawing of one variation of an exemplary control unit that may be used in conjunction with aspects of the present invention. FIG. 2A shows several exemplary features of control portion 10, including a handle 11 and a thumb loop 12 for interacting with the user. Generally, the user may grasp the handle 11, place his thumb inside the thumb loop 12 and squeeze. This and/or similar motions generally affect a mechanical response in the control cylinder 100, also shown in FIG. 2A, which transmits the mechanical response to another portion of the device referred to as a "slave portion" (not shown). The overforce mechanism would, for example, be a portion attached to or in the vicinity of the control cylinder, as shown in FIG. 2A. In addition to the control cylinder 100, certain variations of the device may include "spool valves" that may be, for example, positioned as shown in FIG. 2A. One purpose of the spool valve, among others, is to control fluid communication between the control cylinder 100 and the slave portion of the device. The control portion 10 in FIG. 2A is purely exemplary of one of the types of control portions that may be used in conjunction with aspects of the present invention. Aspects of the present invention may be used in conjunction with a variety of other devices, including different control portions.

Figure 2B:
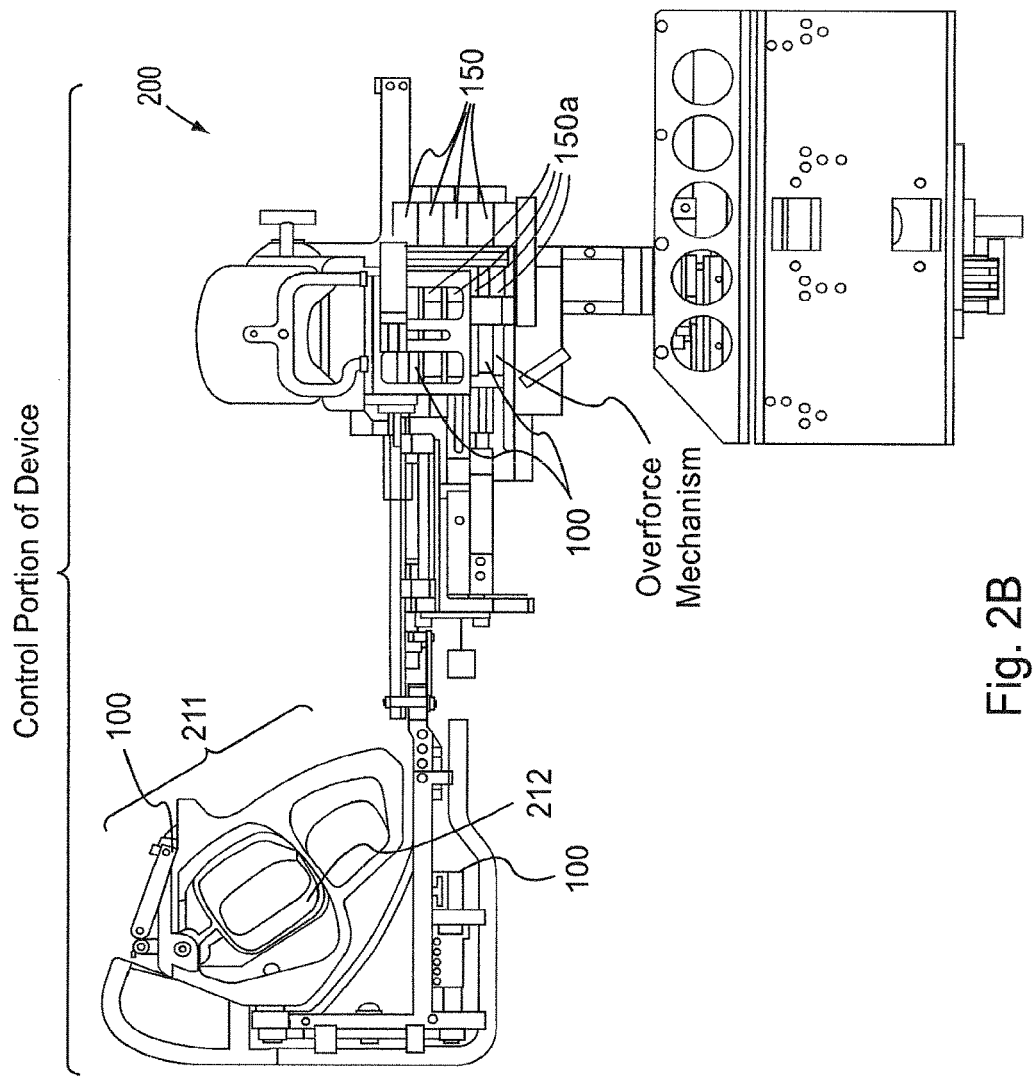
FIG. 2B is a detailed drawing of another aspect of an exemplary control unit that may be used in conjunction with aspects of the present invention.

FIG. 2B is a detailed drawing of another variation of an exemplary control unit that may be used in conjunction with aspects of the present invention. FIG. 2B shows several exemplary features of control portion 200, including a handle 211 and a trigger loop 212 for interacting with the user. The control portion 200 differs from the exemplary control portion 10 shown in FIG. 2A mainly in that it allows more degrees of freedom in the motions that may be transmitted from the user to the slave portion of the device. Each degree of freedom corresponds to its own control cylinder 100, as shown in FIG. 2B. As shown in FIGS. 2A and 2B, the overforce mechanism may be part of a control cylinder. Each may be implemented on several portions of the device simultaneously. Generally, the user may grasp the handle 211, place the user's fingers inside the trigger loop 212, squeeze the trigger loop 212 and move the handle 211 in various directions. This and/or similar motions generally affect a mechanical response in the control cylinders 100, which transmit the mechanical response to the slave portion of the device (not shown). The responses may be mediated by the overforce mechanism, in accordance with aspects of the instant invention. FIG. 2B also shows exemplary spool valves 150 connected to control cylinders 100. As shown in FIG. 2B, the spool valves 150 are generally connected to each of the control cylinders 100. In FIG. 2B, the fluid connections between the exemplary spool valves 150 and the slave portion of the device, inlets 150a, are explicitly shown. Generally, a hydraulic line may be connected to one end of inlets 150a, the other end of which may be connected to a corresponding control cylinder (not shown) on the control or slave portion of the device. In this and other exemplary configurations, each degree of freedom generally has one control cylinder in the control portion and one control cylinder in the respectfully associated slave portion. Control portion 200 in FIG. 2B is purely exemplary of one of the types of control portions that may be used in conjunction with aspects of the present invention. Aspects of the present invention may be used in conjunction with a variety of other devices, including different control portions.

Figure 3:
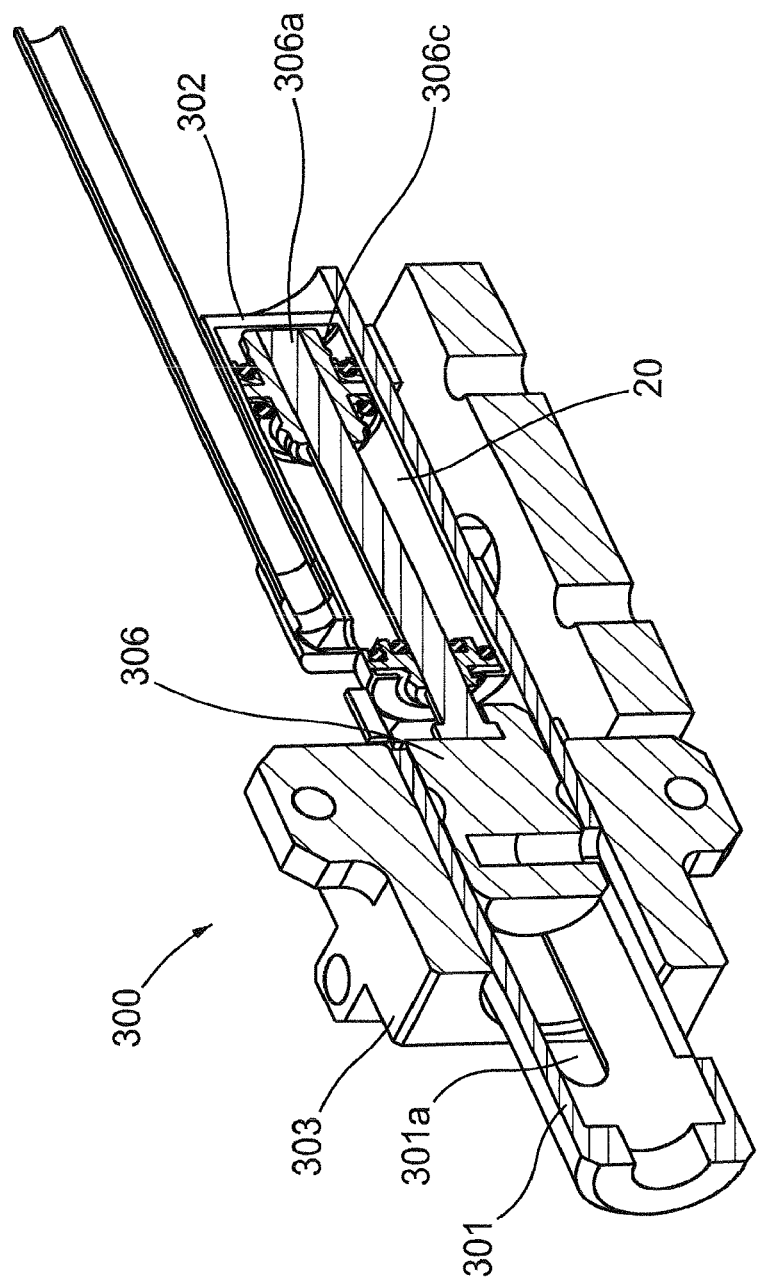
FIG. 3 is a partial cutaway view of an exemplary overforce mechanism.

FIGS. 3 to 7 illustrate an exemplary overforce mechanism 300 that may be used in accordance with aspects of the present invention. The overforce mechanism includes a driving assembly, a driven assembly, and a variably engageable coupling, which are described in detail below. The driving assembly is the portion of the overforce member operatively coupled with the control portion 5. Referring to FIG. 3, which shows a partial cutaway view of the overforce mechanism includes a cradle 301 for receiving a rod 306 and a cylinder 302, The overforce mechanism further comprises an overforce slide mechanism 303, including biasing mechanisms 304 (FIGS. 4 to 5B), such as springs, and coupling members 305 (FIGS. 4 to 6), such as ball bearings, among other things, serves to mechanically couple and de-couple the overforce rod 306 to the overforce slide 303. As shown in FIG. 3, the cylinder 302 rests within the cradle 301. A shaft 306a is slideably provided within the cylinder 302. As seen in FIG. 3, one end of the shaft 306a extends from the cylinder 302 and mates with the rod 306, while the other end of the rod 306a is coupled with a piston 306c. Therefore, because of the mating of the rod 306 with the shaft 306a, movement of the rod 306 produces sliding of the shaft 306a and piston 306c axially within the cylinder 302. The cylinder 302 further comprises hydraulic fluid 20 which is displaced as the piston 306a moves within the cylinder 302.

As will be described in more detail below, the conditions in which the rod 306 and the overforce slide 303 are coupled and de-coupled to one another will be referred to as the "engaged operation" of the apparatus below. FIGS. 5A and 5B show the exemplary overforce mechanism 300 of FIGS. 3 and 4 in a cross-sectional view, in engaged and disengaged operations respectively.

As also shown in FIG. 5A, hydraulic fluid 20 may be disposed in the cylinder 302. The hydraulics of the exemplary overforce mechanism 300 shown in FIGS. 4, 5A and 5B may be substantially similar as described in more detail in U.S. Pat. No. 6,607,475. In particular, FIG. 5A shows the hydraulic fluid 20 contained in the cylinder 302. Hydraulic fluid 20 can exit the cylinder 102 through an inlet, which may create hydraulic pressure at a point in the distal end of the device. Additional hydraulic fluid 20, displaced from a slave cylinder, may enter in to the back of the piston 306c through another inlet, thereby keeping the volume of the hydraulic fluid 20 in the system constant. It is within the scope of aspects of the present invention that alternative hydraulic arrangements may be utilized. For example, hydraulic fluid 20 may be located differently with respect to the inner cylinder 302 or contained in ancillary vessels (not shown). There may be additional hydraulic lines and connections not shown in the Figures, and additional components may be added or removed without altering the nature of aspects of the invention.

Figure 4:
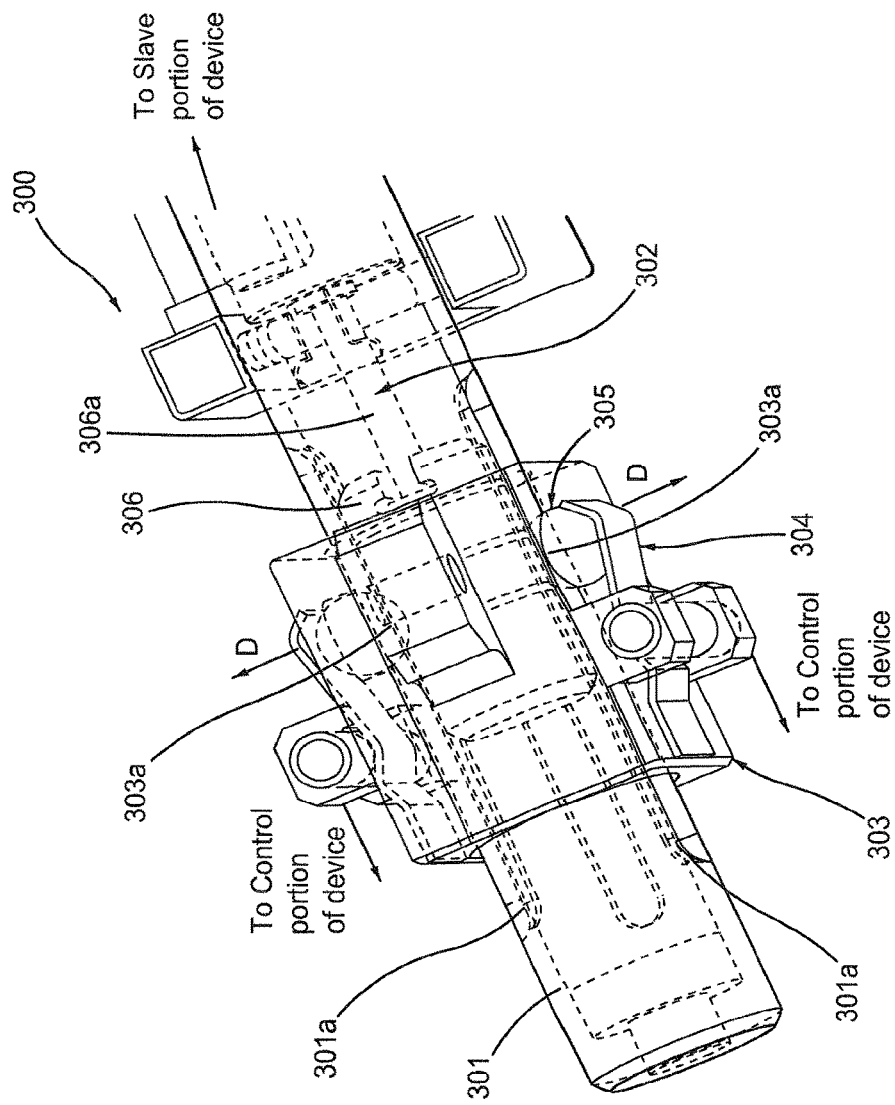
FIG. 4 is a diagram of an exemplary overforce mechanism in engaged mode in accordance with aspects of the present invention.
Figure 5A:
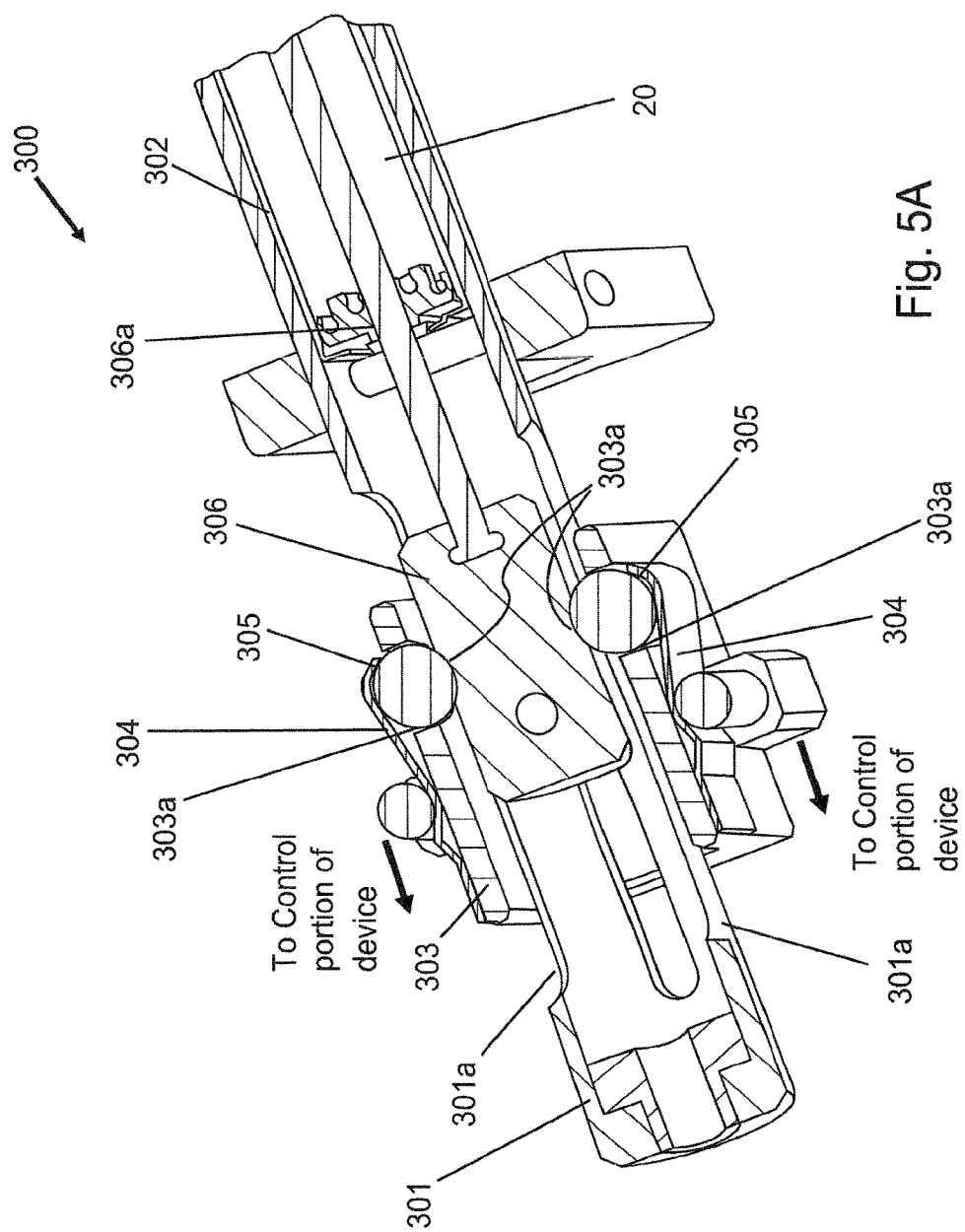
FIGS. 5A and 5B show the exemplary overforce mechanism of FIG. 4 in a cut-away view, in engaged and disengaged operations respectively, in accordance with aspects of the present invention.
Figure 5B:
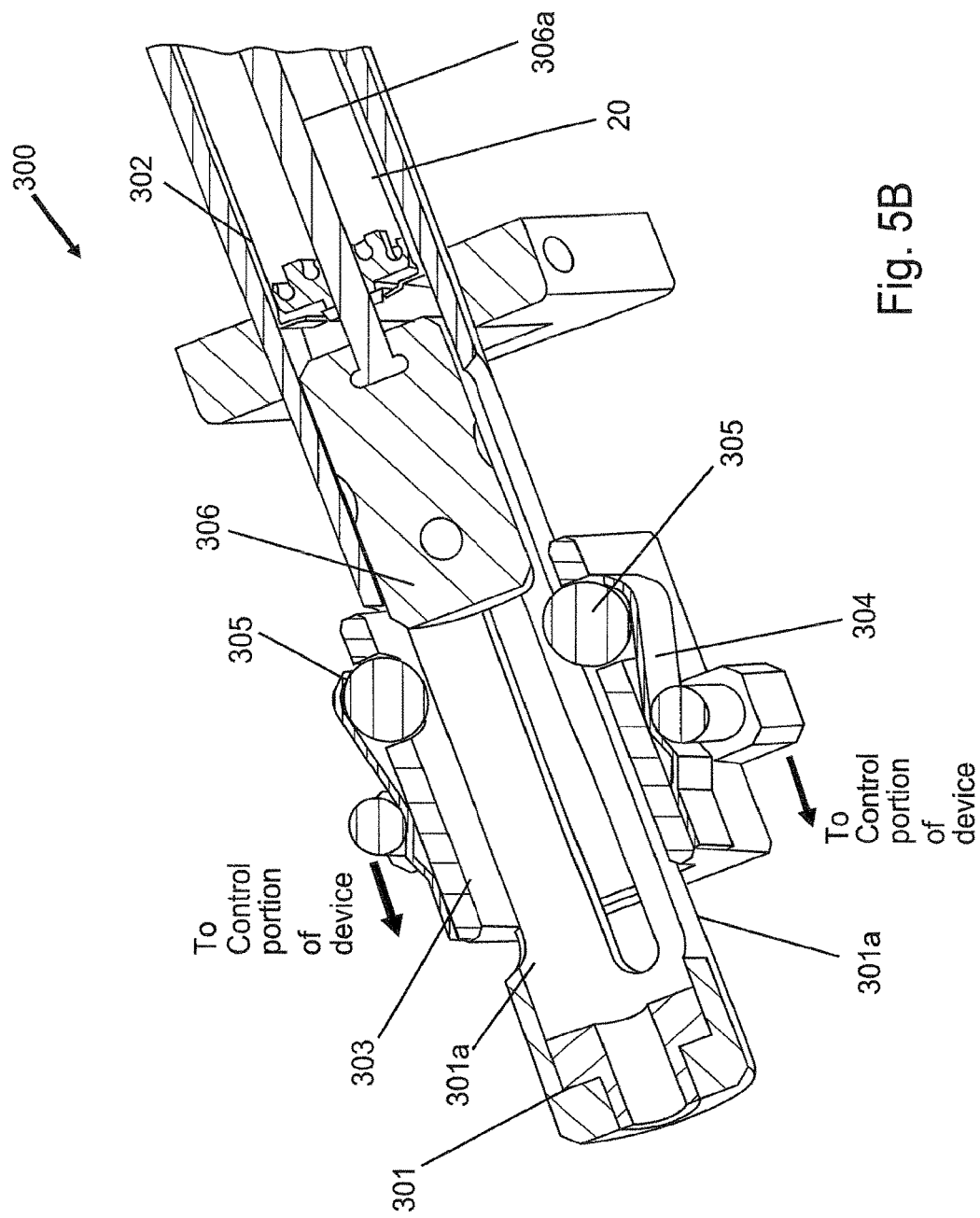

FIGS. 4, 5A and 5B show one exemplary implementation of the overforce mechanism 300. As shown in FIGS. 4, 5A and 5B, the variably engageable coupling may include the overforce slide 303 and various mechanical components to couple the overforce slide to the overforce rod 306, which is attached to the shaft 306a of the cylinder 302. For example, the overforce mechanism 300 may include, as shown in FIGS. 4, 5A and 5B, a set of ball bearings 305 that ride in a track 301a, or guiding portion, in the cradle 301, and the biasing mechanism (304). The driven assembly includes the portion of the overforce mechanism that is driven by the driving assembly, such as the rod 306 and the shaft 306a.

Figure 6:
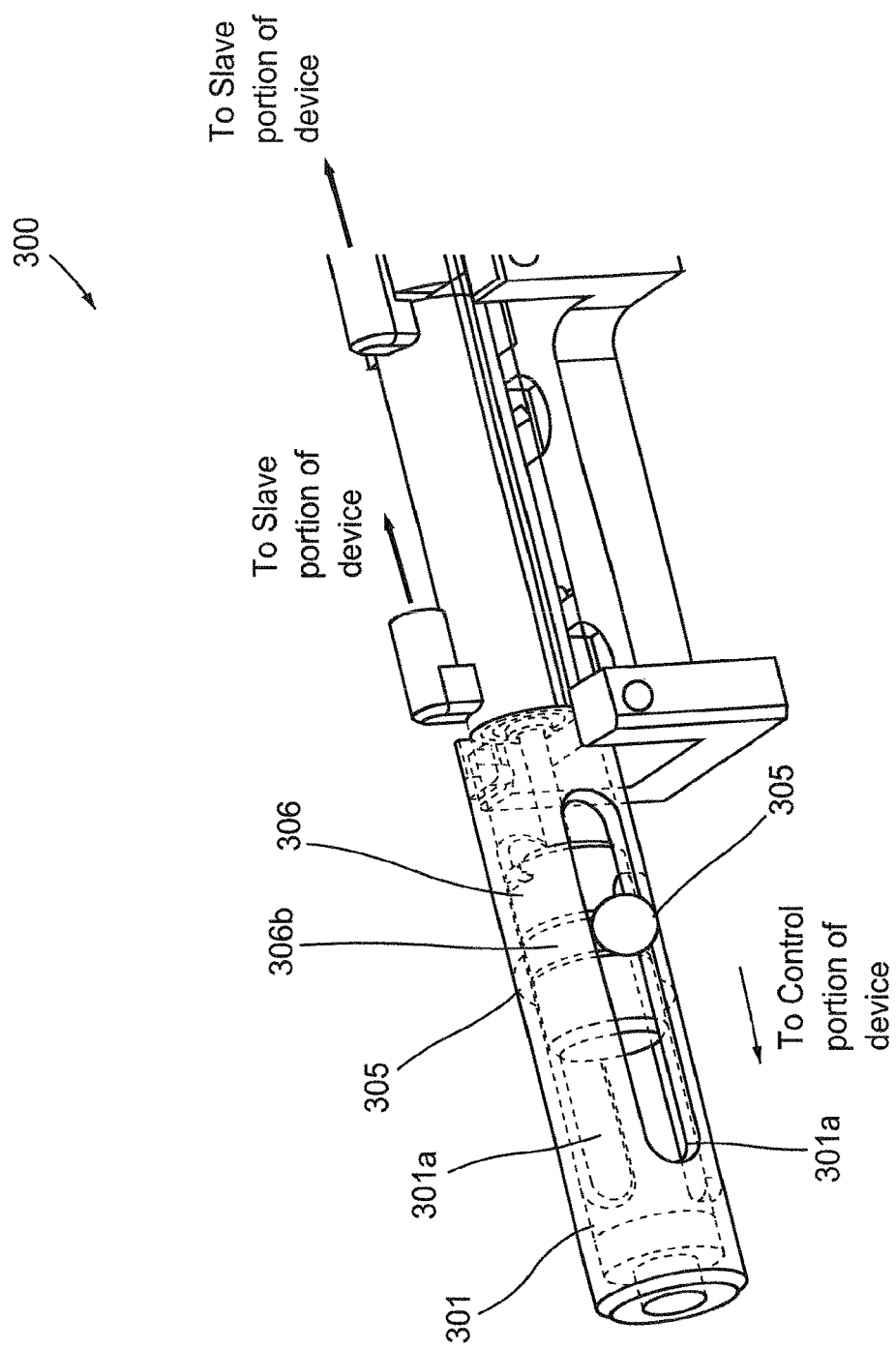
FIG. 6 is a close-up of a partially transparent view of the relationship between the balls of the exemplary overforce mechanism and the depression in the overforce rod 306, shown in FIGS. 5A and 5B, without the overforce slide, in accordance with aspects of the present invention.
Figure 7:
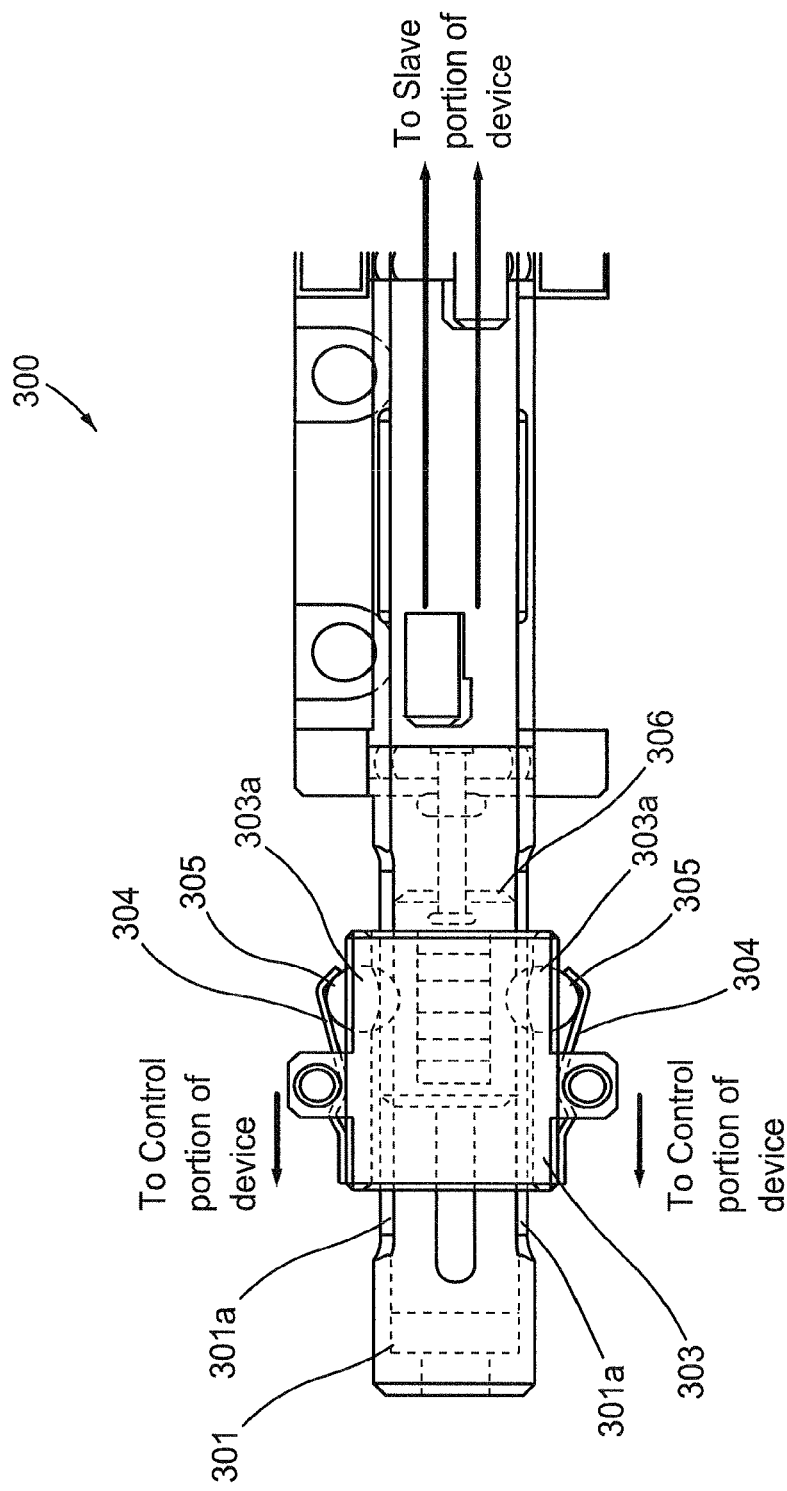
FIG. 7 is a schematic, partially transparent side view of the exemplary overforce mechanism of FIG. 4 in engaged mode, in accordance with aspects of the present invention.

The ball bearings 305 may make contact with the other portions of the device via holes 303a in the overforce slide 303. In addition, there may be a channel or depression 306b in the overforce rod 306 sized to accommodate at least a portion of the ball bearings 305. FIG. 6 is a close-up partially transparent view of the relationship between the ball bearings 305 of the exemplary overforce mechanism 300 and the depression 306b in the overforce rod 306, without the overforce slide 303 being visible. FIG. 7 is a schematic, partially transparent side view of the exemplary overforce mechanism of FIGS. 3 and 4 in engaged mode in accordance with aspects of the present invention. As shown in FIGS. 6 and 7, the ball bearings 305 may be held in the depression 306b via the springs 304. When the ball bearings 305 are retained in place via the biasing features 304 through the retention features 303a in the overforce slide 303, the coupling members 305, such as ball bearings, may mechanically couple the overforce slide 303 and the overforce rod 306. In other words, when the ball bearings 305 are fixed in the depression 306b by the springs 304, the overforce slide 303, the overforce rod 306, and the piston 306c may move as a single unit. Thus the force applied to the overforce slide 303 is releasably connected to the overforce rod 306, which is attached to the shaft 306a, and thereby causes motion of the piston 306b in order to pump hydraulic fluid 20 to and from slave cylinders. This is merely one exemplary implementation and that other implementations in accordance with aspects of the present invention are also possible. For example, alternatively, the ball bearings 305 may be fixed in the reverse sense, such that there are openings in the overforce rod 306 and a depression in the overforce slide 303. In this case, the spring 304 may be fixed onto or inside the overforce rod 306 instead of, or in addition to, on the overforce slide 303, as shown in FIGS. 4, 5A and 5B. If the overforce mechanism is fixed in the reverse sense, its operation may be substantially the reverse of that described in the following paragraphs.

In engagement operation, as shown in FIGS. 4 and 5A, when the ball bearings 305 are positioned such that they are inside the depression 306b of the overforce rod 306, as shown in FIGS. 5A, 6 and 7, they may transmit motion of the slide 303 to the overforce rod 306 and the piston 306c. In other words, the coupling provided by the ball bearings 305 may allow the overforce rod 306, the piston 306b and the overforce slide 303 move as a single unit. When the user imparts a force greater than a threshold set by a spring force of the spring 304, the force imparted to the ball bearings 305 by the overforce rod 306 may press outwardly on the springs 304 to such an extent that the balls overcome the force of the springs 304, resulting in the breaking of the coupling provided by the ball bearings 305. In this situation, referred to as "disengaged operation," the mechanical coupling of the overforce rod 306 and the slide 303 may be broken. As such, the spring 304 may be selected to have a desired spring force corresponding to a force threshold that disengages the coupling provided by the ball bearings 305, thereby activating the disengaged operation and halting a transfer of force or motion to the slave portions and/or end effectors or tools of the device.

Engaged operation is defined as when force imparted by the user to the exemplary overforce mechanism 300 is insufficient to overcome the force of the spring 304. Generally, in engaged operation, most or all of the mechanical motion performed by the user may be transmitted by the user through the system to the target or operating theater. In this situation, the ball bearings 305 may remain fixed with respect to the overforce slide 303 in the position shown in FIG. 4. In other words, the overforce rod 306 and the slide 303 may move as one unit. Alternatively, ordinary conditions may be defined such that the overforce slide 303 and the overforce rod 306 allow some motion relative to one another.

In engaged operation, upon squeezing the thumb loop, for example, the overforce mechanism 300 may be actuated through a series of levers and gears, as described in more detail in U.S. Pat. No. 6,607,475, from the retracted position to the extended position. In engaged operation, the ball bearings 305 may be centrally located within the depression 306b of the overforce rod 306, as shown in FIG. 5A, and may remain fixed with respect to the depression 306b. In this manner, among others, the control portions 5 may use the exemplary overforce mechanism 300 to channel the mechanical force from the user to the application. Generally speaking, devices actuated by the exemplary overforce mechanism 300 are referred to as the "slave" portion of the device. These devices may include mechanical grippers, lever arms, pivoting devices, translating devices, swiveling devices, cutting tools, grasping tools and any other suitable devices. The mechanical force can be used in any number of suitable ways by the slave portion of the devices. For example, control portions 5 can be used to conduct surgical procedures, move objects or to mechanically provide force for any suitable number of applications. As shown in FIG. 1A, control portions 5 may be coupled to various surgical apparatus (e.g., clamps, shears, needles, etc.) for performing a surgical operation.

However, when the thumb loop is actuated too quickly or too severely by the user, the overforce mechanism 300 may actuate portions of the slave portion of the device in such a manner as to cause damage either to the device itself or elsewhere (as described above). In this case, the exemplary overforce mechanism 300 may enter disengaged operation such that the overforce slide 303 is decoupled from the overforce rod 306 in the manner described below. FIG. 5B shows the exemplary overforce mechanism of FIG. 5B in disengaged operation.

Disengaged operation may be initiated when the impulse (i.e., applied force over a unit time) from the user in the control portion of the device is large enough to dislodge the ball bearings 305 from the depression 306b in the overforce rod 306. As shown in FIG. 5B, in disengaged operation, the ball bearings 305 may become dislodged from the depression 306b when, among other things, there is too much force applied, such that the ball bearings 305 move with respect to the depression 306b. When the ball bearings 305 move with respect to the depression 306b, they may be forced outwardly with respect to the overforce rod 306 by the contours of the depression 306b. The outward motion of the ball bearings 305 may be generally along direction D shown in FIG. 4 and may cause the ball bearings 305 to press on the spring 304 with a force that may be so large as to overcome a spring force. Once the spring force is overcome, the ball bearings 305 may slide free of the depression 306b of the overforce rod 306. This action may de-couple the overforce slide 303 from the overforce rod 306 and the rest of the exemplary overforce mechanism 300 such that user motion is no longer transmitted. If user motion is not transmitted in disengaged operation, the motion may not be transmitted hydraulically to other portions of the device, including the slave portion of the device. In this situation, the overforce slide 303 may slide freely with respect to the overforce rod 306 in response to the user input. In this way, the motion of the user is not transmitted by the device and the slave portions of the device (not shown) do not react to the user input.

Figure 8:
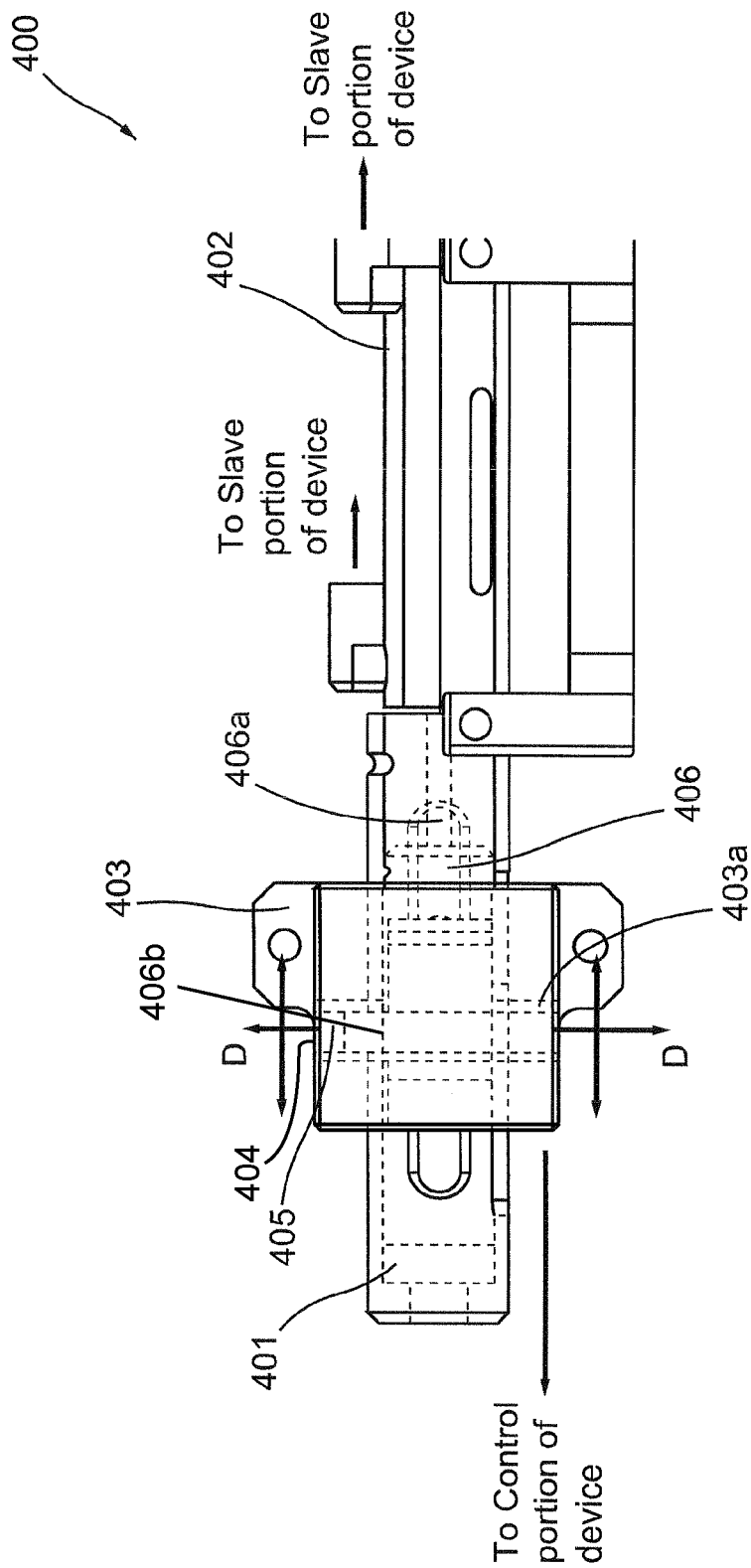
FIG. 8 is a schematic of another exemplary overforce mechanism of FIG. 4 in engaged mode, in accordance with aspects of the present invention.

FIG. 8 shows another exemplary implementation of an overforce mechanism, in accordance with aspects of the present invention. As shown in FIG. 8, the overforce slide 403 of the overforce mechanism 400 may be substantially similar to the overforce slide 303 of the exemplary overforce mechanism 300. However, the mechanical components for coupling the overforce slide 403 to the shaft 401 and the cylinder 402 may be different. For example, the overforce mechanism 400 may include, as shown in FIG. 8, a spring 404 that holds a dowel 405 in contact with the overforce rod 406.

The dowel 405 may make contact with the other portions of the device via a dowel-accommodation opening 403a in the overforce slide 403. The dowel 405 may be held, via the spring 404, in contact with the overforce rod 406, as shown in FIG. 8, similarly to the way the ball bearings 305 are sandwiched between spring 304 and overforce rod 306 shown in FIG. 5A. In addition, there may be a depression 406b in the overforce rod 406 that accommodates at least a portion of dowel 405. The depression 406b may be, for example, substantially similar to the depression 306b in the overforce rod 306 shown in FIG. 6.

As best shown in FIG. 8, the dowel 405 may be pressed or fixed into the depression 406b by a spring force supplied via the spring 404. When the dowel 405 is pressed into place by spring 404 through the dowel-accommodation opening 403a in the overforce slide 403, the dowel 405 may mechanically couple the overforce slide 403 and the overforce rod 406. In other words, when the dowel 405 is fixed in the depression 406b by spring 404, the overforce slide 403 and the overforce rod 406 may move as a single unit. This is merely one exemplary implementation and that other implementations in accordance with aspects of the present invention are also possible. For example, the dowel 405 may be, alternatively, fixed in the reverse sense such that there are openings in the in the overforce rod 406 and a depression in the overforce slide 403. In this case, the spring 304 may be fixed onto or inside the overforce rod 406 instead of, or in addition to, on the overforce slide 403, as shown in FIG. 8. If the overforce mechanism is fixed in the reverse sense, its operation may be substantially the reverse of that described in the following paragraphs.

In engagement operation, as shown in FIG. 8, when the dowel 405 is positioned such that it is inside the depression 406b of the overforce rod 406, it may transmit motion of the overforce rod 406 to the shaft 406a. In other words, because of the coupling provided by the dowel 405, the overforce rod 406 and the overforce slide 403 may move as a single unit. When the user imparts a force greater than a threshold set by the spring 404, the force imparted to the dowel 405 by the overforce rod 406 may press outwardly on the spring 404 to such an extent that the dowel 405 may overcome a force of the spring 404. In this situation, referred to as "disengaged operation," the mechanical coupling of the overforce rod 406 and the overforce slide 403 may be broken.

Engaged operation is defined as when a force imparted by the user to the exemplary overforce mechanism 400 is insufficient to overcome the force of the spring 304. Generally, in engaged operation, most or all of the mechanical motion performed by the user may be transmitted by the user through the system to the target or operating theater. In this situation, the dowel 405 may remain fixed with respect to the overforce slide 403 in the position shown in FIG. 8. In other words, the overforce slide 403 and overforce rod 406 (and thus the shaft 406*a*) may move as one unit.

In engaged operation, upon squeezing the thumb loop, for example, the overforce mechanism 400 may be actuated through a series of levers and gears, as described in more detail in U.S. Pat. No. 6,607,475, from the retracted position to the extended position. In engaged operation, the dowel 405 may be centrally located within the depression 406*b* of the overforce rod 406 and remains fixed with respect to the depression 406*b*. In this manner, among others, control portions 5 use the exemplary overforce mechanism 400 to channel the mechanical force from the user to the application. Generally speaking, devices actuated by the exemplary overforce mechanism 400 are referred to as the "slave" portion of the device. These devices may include mechanical grippers, lever arms, pivoting devices, translating devices, swiveling devices, cutting tools, grasping tools and any other suitable devices. The mechanical force may be used in any number of suitable ways by the slave portion of the devices. For example, the control portions 5 may be used to conduct surgical procedures, move objects or to mechanically provide force for any suitable number of applications. As shown in FIG. 1A, the control portions 5 may be coupled to various surgical apparatus (e.g., clamps, shears, needles, etc.) for performing a surgical operation.

However, when the thumb loop is actuated too quickly or too severely by the user, a danger may arise in that the overforce mechanism 400 may actuate portions of the slave portion of the device in such a way as to cause damage either to the device itself or elsewhere (as described above). In this case, the overforce mechanism 400 may enter a disengaged operation, such that the overforce slide 403 mechanism decouples the inner and outer cylinders 402 and 401 in the manner described below. Although not shown, disengagement operation for the exemplary overforce mechanism 400 may be substantially similar to disengagement operation of the exemplary overforce mechanism 300 shown in FIG. 5B.

Disengaged operation may be initiated when the impulse (i.e., applied force over a unit time) from the user in the control portion of the device is large enough to dislodge the dowel 405 from the depression 406*b* in the overforce rod 406. In disengaged operation, the dowel 405 may become dislodged from the depression 406*b* when, for example, there too much force applied to the overforce rod 406 such that the dowel 405 moves with respect to the depression 406*b*. When the dowel 405 moves with respect to the depression 406*b*, it may be forced outwardly with respect to the overforce rod 406 by the contours of the depression 406*b*. The outward motion of the dowel 405 may generally be along direction D shown in FIG. 8 and may cause the dowel 405 to press a the spring or other restoring force member (not shown) with a force is so large as to overcome, for example, a spring force. If the spring force is overcome, the dowel 405 may slide free of the depression 406*b* of the overforce rod 406 and through the dowel-accommodation opening 403*a* of the overforce slide 403. This motion of the dowel may de-couple the overforce slide 403 from the overforce rod 406 and the rest of the exemplary overforce mechanism 400 such that user motion is no longer transmitted. In this situation, the overforce slide 403 may slide freely in response to the user input, while the cylinder shaft 401 and the overforce rod 406 may remain fixed. In this way, the motion of the user may not be transmitted by the device, and the slave portions of the device (not shown) do not react to the user input.

Although aspects of the invention have been described with reference to various aspects of the present invention and examples with respect to a surgical instrument, it is within the scope and spirit of the invention to incorporate use with any suitable mechanical device. Further, while the invention has been described with reference to a surgeon, the invention may be used by another user, depending on circumstances in which the invention is used. Additionally, while the invention has been described using hydraulic mechanisms, it is within the scope of the invention that non-hydraulic mechanisms may be implemented, such as cable-pulley or push-pull cable devices. Thus, it should be understood that numerous and various modifications may be made without departing from the spirit of the invention.

What is claimed is:

1. An overforce mechanism for a surgical system component, comprising:
   a mechanically actuated driving assembly;
   a driven assembly drivable by the driving assembly;
   a cradle having at least one guiding portion, the guiding portion including a track defined in the cradle; and
   a variably engageable coupling configured to variably connect operation of the driving assembly to the driven assembly, the variably engageable coupling comprising:
   a slide moveable in a first direction, the slide variably engageable with the driven assembly and directly engaged by the driving assembly;
   at least one coupling member protruding from the driven assembly; and
   a biasing mechanism for varying the variable engagement of the slide with the driven assembly,
   wherein the at least one coupling member is configured to move relative to the guiding portion and configured to impart an outward force on the biasing member in a second direction, the outward force moving the biasing member in the second direction above a preset force limit, the second direction being perpendicular to the first direction;
   the variably engageable coupling being configured to communicate motion directly from the driving assembly to the driven assembly below the preset force limit and to disable communication of motion from the driving assembly to the driven assembly above the preset force limit.

2. The overforce mechanism of claim 1,
   wherein the at least one coupling member is engageable with the slide via at least a first retention feature and the at least one guiding portion,
   wherein the first retention feature is partially defined in the slide, and
   wherein the biasing mechanism is engageable with the at least one coupling member and imparts a retaining force on the at least one coupling member.

3. The overforce mechanism of claim 2, wherein the driven assembly further comprises a rod mateable with a shaft and at least a second retention feature being partially defined in the rod, and the slide being coupled with the rod via the at least one coupling member.

4. The overforce mechanism of claim 3, wherein the biasing mechanism biases the at least one coupling member to engage with the rod.

5. The overforce mechanism of claim 2, wherein the at least one coupling member comprises a pair of ball bearings.

6. The overforce mechanism of claim 2, wherein the at least one coupling member comprises a dowel.

7. The overforce mechanism of claim 2, wherein the at least one guiding portion is mateably engageable with the at least one coupling member.

8. The overforce mechanism of claim 3, wherein the retaining force of the biasing mechanism is greater than the outward force imparted by the at least one coupling member during a sliding operation of the slide when the outward force is less than or equal to a threshold force, thereby maintaining engagement of the at least one coupling member with the rod.

9. The overforce mechanism of claim 3, wherein the retaining force of the biasing mechanism is less than the outward force imparted by the at least one coupling member during the sliding operation of the slide when the outward force is greater than a threshold force, thereby disengaging the at least one coupling member from the rod.

10. The overforce mechanism of claim 1, wherein the surgical system is mechanically operated via hydraulic pressure.

11. A hydraulically driven surgical system, comprising:
a control portion having at least one control cylinder;
an actuation portion;
a slave portion hydraulically connected to the control portion, the slave portion having at least one slave cylinder corresponding to the at least one control cylinder and at least one surgical tool; and
an overforce mechanism operatively connected with the control portion,
wherein actuation of the actuation portion transmits a mechanical force to the slave portion via the driven assembly, the overforce mechanism including:
a mechanically actuated driving assembly;
a driven assembly drivable by the driving assembly;
a cradle having at least one guiding portion, the guiding portion including a track defined in the cradle; and
a variably engageable coupling comprising:
a slide moveable in a first direction, the slide variably engageable with the driven assembly and directly engaged by the driving assembly;
at least one coupling member protruding from the driven assembly; and
a biasing mechanism for varying the variable engagement of the slide with the driven assembly,
wherein the at least one coupling member is configured to move relative to the guiding portion and configured to impart an outward force on the biasing member in a second direction, the outward force moving the biasing member in the second direction above a preset force limit, the second direction being perpendicular to the first direction;
the variably engageable coupling configured to variably connect operation of the driving assembly to the driven assembly, the variably engageable coupling being configured to communicate motion directly from the driving assembly to the driven assembly below the preset force limit and to disable communication of motion from the driving assembly to the driven assembly below the preset force limit.

12. The hydraulically driven surgical system of claim 11,
wherein the at least one coupling member is engageable with the slide via at least a first retention feature and the at least one guiding portion,
wherein the first retention feature is partially defined in the slide, and
wherein the biasing mechanism is engageable with the at least one coupling member and imparts a retaining force on the at least one coupling member.

13. The hydraulically driven surgical device of claim 12, further comprising a rod mateable with a shaft, wherein a second retention feature is partially defined in the rod, and wherein the slide is coupled with the rod via the at least one coupling member.

14. The hydraulically driven surgical device of claim 13, wherein the biasing mechanism biases the at least one coupling member to engage with the rod.

15. The hydraulically driven surgical device of claim 13, wherein the retaining force of the biasing mechanism is greater than the outward force imparted by the at least one coupling member during a sliding operation of the slide when the outward force is less than or equal to a threshold force, thereby maintaining engagement of the at least one coupling member with the rod.

16. The hydraulically driven surgical device of claim 13, wherein the retaining force of the biasing mechanism is less than the outward force imparted by the at least one coupling member during the sliding operation of the slide when the outward force is greater than a threshold force, thereby disengaging the at least one coupling member from the rod.

17. The hydraulically driven surgical device of claim 12, wherein the at least one coupling member comprises a pair of ball bearings.

18. The hydraulically driven surgical device of claim 12, wherein the at least one coupling member comprises a dowel.

19. The hydraulically driven surgical device claim 12, wherein the at least one guiding portion is mateably engageable with the at least one coupling member.

20. The hydraulically driven surgical system of claim 11, wherein the actuation portion of the control portion comprises a handle and a trigger.

21. The hydraulically driven surgical device of claim 11, further comprising a spool valve for controlling fluid communication between the at least one control cylinder and the at least one slave cylinder.

22. The hydraulically driven surgical device of claim 11, wherein the at least one control cylinder comprises a plurality of cylinders, and wherein each control cylinder of the plurality of control cylinders provides a degree of freedom for moving the slave portion.

23. A method of operating a hydraulically driven surgical device having an overforce mechanism, the overforce mechanism including a mechanically actuated driving assembly, a driven assembly drivable by the driving assembly, a cradle having at least one guiding portion, the guiding portion including a track defined in the cradle, and a variably engageable coupling, the method comprising:
operatively connecting the driving assembly to a control portion;
configuring the variably engageable coupling to variably connect operation of the driving assembly to the driven assembly; and
configuring the variably engageable coupling to communicate motion directly from the driving assembly to the driven assembly below a preset force limit and to disable communication of motion from the driving assembly to the driven assembly above the preset force limit, wherein the variably engageable coupling comprises:

a slide moveable in a first direction, the slide variably engageable with the driven assembly and directly engaged by the driving assembly;

at least one coupling member protruding from the driven assembly; and a biasing mechanism for varying the variable engagement of the slide with the driven assembly, wherein the at least one coupling member is configured to move relative to the guiding portion and configured to impart an outward force on the biasing member in a second direction, the outward force moving the biasing member in the second direction above the preset force limit, the second direction being perpendicular to the first direction.

24. The method of claim 23, further comprising transmitting a mechanical force to a slave portion of the hydraulically driven surgical device via the driven assembly below the preset force limit.

25. The method of claim 23, wherein actuating the control portion comprises actuating a handle and a trigger.

* * * * *